US007767823B2

(12) United States Patent
McKnight et al.

(10) Patent No.: US 7,767,823 B2
(45) Date of Patent: Aug. 3, 2010

(54) PROCESS FOR THE PURIFICATION OF A SALT OF CLAVULANIC ACID

(75) Inventors: John McKnight, Braughing (GB); Guo Zhang, Worthing (GB)

(73) Assignee: SmithKline Beecham Limited, Brentford, Middlesex (GB)

(*) Notice: Subject to any disclaimer, the term of this patent is extended or adjusted under 35 U.S.C. 154(b) by 1633 days.

(21) Appl. No.: 10/275,852

(22) PCT Filed: May 9, 2001

(86) PCT No.: PCT/GB01/02025

§ 371 (c)(1), (2), (4) Date: Oct. 27, 2005

(87) PCT Pub. No.: WO01/87891

PCT Pub. Date: Nov. 22, 2001

(65) Prior Publication Data

US 2006/0079676 A1 Apr. 13, 2006

(30) Foreign Application Priority Data

May 13, 2000 (GB) .................... 0011519.6
May 13, 2000 (GB) .................... 0011521.2

(51) Int. Cl.
*C07D 277/60* (2006.01)
*C07D 277/62* (2006.01)

(52) U.S. Cl. ...................................... 548/152

(58) Field of Classification Search .............. None
See application file for complete search history.

(56) References Cited

U.S. PATENT DOCUMENTS 5,821,364 A * 10/1998 Weber .................. 540/349

FOREIGN PATENT DOCUMENTS

| AT | 400 846 | 3/1996 |
|----|---------|--------|
| DE | 37 29 338 | 3/1989 |
| EP | 0 026 044 | 4/1981 |
| EP | 0 277 008 | 8/1988 |
| EP | 0 312 813 | 4/1989 |
| EP | 0 532 341 | 3/1993 |
| EP | 0 594 099 | 4/1994 |
| EP | 077008 | * 7/1998 |
| EP | 1284978 | 8/2004 |
| FR | 1 299 883 | 12/1962 |
| GB | 1 508 977 | 4/1975 |
| GB | 2 003 863 | 3/1979 |
| GB | 2 204 944 | 9/1993 |
| GB | 2264944 | * 9/1993 |
| GB | 2 287 025 | 9/1995 |
| WO | WO 93 08287 | 4/1993 |
| WO | WO 93 25557 | 12/1993 |
| WO | WO 94 21647 | 9/1994 |
| WO | WO 95 04148 | 2/1995 |
| WO | WO 95 23870 | 9/1995 |
| WO | WO 95 34194 | 12/1995 |
| WO | WO 96 20199 | 7/1996 |
| WO | WO 96 28452 | 9/1996 |
| WO | WO 96 33197 | 10/1996 |
| WO | 97/05142 | 2/1997 |
| WO | 98/21212 | 5/1998 |
| WO | WO 98/21212 | 5/1998 |
| WO | 98/23622 | 6/1998 |
| WO | WO 98/23622 | 6/1998 |
| WO | 98/42858 | 10/1998 |
| WO | 98/48036 | 10/1998 |
| WO | WO 98/42858 | 10/1998 |
| WO | WO 00 04028 | * 1/2000 |

OTHER PUBLICATIONS

EP 1284978 Opposition papers, filed Aug. 18, 2004.

* cited by examiner

*Primary Examiner*—James O Wilson
*Assistant Examiner*—Noble Jarrell
(74) *Attorney, Agent, or Firm*—Dara L. Dinner; Theodore R. Furman

(57) ABSTRACT

A process in which a salt of clavulanic acid, typically an amine salt or an alkali metal salt is exposed to conditions, particularly a pH of less than 6.0, which reduces the quantity of contaminating impurities. The process may be a washing process, a recrystallisation process or a preparative process.

16 Claims, No Drawings

PROCESS FOR THE PURIFICATION OF A SALT OF CLAVULANIC ACID

This invention relates to novel processes for the preparation of salts of clavulanic acid in a more pure state.

Clavulanic acid (Z)-(2R,5R)-3-(2-Hydroxyethylidene)-7-oxo-4-oxa-1-azabicyclo[3.2.0]heptane-2-carboxylic acid) is a β-lactamase inhibitor which is used commercially as a component of pharmaceutical formulations, usually in the form of its pharmaceutically acceptable salts, particularly potassium clavulanate. Clavulanic acid is produced commercially by culture of the microorganism *Streptomyces clavuligerus*, for example as described in GB 1508977.

Clavulanic acid may be extracted from the culture medium in various ways. Normally the cells of the *S. clavuligerus* are first removed from the culture medium by such methods as filtration or centrifugation before such extraction procedures are commenced. The clavulanic acid may be extracted from this clarified culture medium by solvent extraction from cold clarified culture medium adjusted to an acid pH. Whole broth extraction is also feasible. In the solvent extraction process the clavulanic acid is extracted into an organic solvent. After separation of the phases clavulanic acid is found in solution in the organic phase.

The clavulanic acid may be back extracted from the organic phase into a new aqueous phase by making use of the greater water solubility of salts of clavulanic acid with organic amines, and isolating such an amine salt from the aqueous phase. In such a process the amine salt is formed as an intermediate in the process of converting crude clavulanic acid into a pharmaceutically acceptable salt. Such a process is described in for example EP-A-0 026 044, in which a solution of impure clavulanic acid in an organic solvent is contacted with t-butylamine to form the t-butylamine salt of clavulanic acid, which is then isolated. Other similar processes are known which use other organic amines, such as tertiary octylamine (see EP-A-0 594 099 (Pharma Development)) diethylamine, tri-(lower alkyl) amines, dimethylaniline and NN'-diisopropyl-ethylenediamine. WO-A-93/25557 (SmithKline Beecham) discloses a very extensive list of amines which can be used in this way. WO-A-94/22873 (Gist Brocades) discloses use of various tertiary, tertiary diamines such as N,N,N',N'-tetramethyl-1,2-diaminoethane, N,N,N',N'-tetramethyl-1,6-diaminohexane, 1,2-dipiperidinoethane and dipiperidinomethane. WO-A-96/20199 (Spurcourt) discloses use of diaminoethers such as bis (2-dimethylaminoethyl) ether. GB-A-2298201 (Spurcourt) discloses use of various benzhydrylamines. WO-A-96/33197 (LEK) discloses use of further amines including symmetrical N,N'-alkylethylene diamines, such as N,N'-diisopropyl-ethylenediamine, N,N'-diethylene diamine, N,N'-dibenzylethylene diamine and N,N,N',N'-tetramethylene diamine. WO-A-98/21212 (Gist-Brocades) for example discloses a process in which the amines N,N,N',N'-tetramethylethylenediamine, 1,3-bis(dimethylamino)-2-propanol, benzhydrylamine and bis (2-(dimethylamino) ethyl) ether are used. WO-A-98/23622 (Biochemie) discloses use of diisopropyl-ethylen-diamine.

After isolation the intermediate amine salt may be converted into a pharmaceutically useful salt of clavulanic acid, particularly an alkali metal salt especially potassium clavulanate, generally by reaction of the intermediate amine salt with a salt precursor compound such as potassium 2-ethylhexanoate.

The fermentation process by which clavulanic acid is prepared also produces side product impurities. A number of such impurities have been identified as peaks in the HPLC trace of crude clavulanic acid, intermediate amine salts and pharmaceutically acceptable salts of clavulanic acid as prepared by conventional processes, but few have been chemically identified. One such impurity has recently been identified by the present inventors as N-succinyl tyrosine.

It is desirable that as little of such impurities as possible are present in the final product pharmaceutically acceptable salt of clavulanic acid, and therefore that such impurities should be removed, either during the isolation of clavulanic acid or from the final product. For example such impurities may be removed from the above-mentioned intermediate amine salt, during the step of conversion of the intermediate amine salt to the pharmaceutically acceptable salt, or from the final salt product.

Successful identification of this impurity as N-succinyl tyrosine has unexpectedly made available processes to prepare salts of clavulanic acid which are contaminated by less N-succinyl tyrosine than has hitherto been possible.

The process may be a purification process in which N-succinyl tyrosine is removed from a salt of clavulanic acid contaminated with it.

Therefore the invention provides a purification process in which a salt of clavulanic acid, contaminated with or believed to be contaminated with N-succinyl tyrosine, is subjected to conditions which are selected to remove N-succinyl tyrosine. Such conditions may be chemical conditions, e.g. treatment with one or more suitable reagent. Suitably the salt of clavulanic acid, contaminated or believed to be contaminated with N-succinyl tyrosine, may be subjected to such conditions by exposure to a liquid medium, e.g. an organic solvent or organic solvent-water mixture, containing such a reagent. Such a process may involve washing of the salt of clavulanic acid in a solid state with such a liquid medium, or crystallisation of the salt of clavulanic acid from such a liquid medium. Alternatively the salt of clavulanic acid, contaminated or believed to be contaminated with N-succinyl tyrosine, may be exposed to a suitable reagent in solid form.

Alternatively the purification process may be a process in which a salt of clavulanic acid, contaminated or believed to be contaminated with N-succinyl tyrosine, is suspended or dissolved in a liquid medium, e.g. an organic solvent or organic solvent-water mixture, and is exposed to a material which is selected to absorb N-succinyl tyrosine and thereby removes N-succinyl tyrosine from the salt.

Alternatively the process may be a preparative process in which the salt of clavulanic acid is prepared under conditions selected to minimise the formation of N-succinyl tyrosine and/or its retention in the product salt of clavulanic acid. For example the salt of clavulanic acid may be prepared in a liquid medium, e.g. an organic solvent, an aqueous medium, or a mixture of an organic solvent, containing reagents which remove N-succinyl tyrosine, or subjected to chemical or physical conditions which remove N-succinyl tyrosine.

The salt of clavulanic acid purified or prepared in the above processes may be an amine salt of clavulanic acid, e.g. with any of the amines referred to above, especially tertiary butylamine, and this amine salt may be subsequently be converted into a final product pharmaceutically acceptable salt of clavulanic acid, such as an alkali metal salt, e.g. potassium clavulanate. Alternatively the salt may be a metal salt of clavulanic acid, for example an alkali metal salt of clavulanic acid, particularly potassium clavulanate.

It has further unexpectedly been discovered that the level of impurities, such as the above-mentioned N-succinyl tyrosine, in a salt of clavulanic acid can reduced if the salt is exposed to a selected range of pH. It is an object of this invention to use this discovery in the provision of improved processes for the preparation of such pharmaceutically acceptable salts.

According to this invention a process is provided comprising exposure of a salt of clavulanic acid to a liquid medium at a pH of less than 6.5, preferably 6.0 or less, more preferably pH 5.5 or less, more preferably pH 5.0 or less, more preferably being above pH 3.5, e.g. pH 3.5-5.5, typically ca. pH 4.5. The term "pH" as used herein includes the conventional usage of the term pH as the logarithm of the reciprocal of the hydrogen ion concentration. Also the term pH as used herein includes the observed pH, i.e. the pH as measured by exposing the medium to a conventional pH meter of known type, suitably calibrated by known methods. Normally the media used in the process of this invention will contain some water.

Treatment of the salt in this way in the process of the invention can reduce the level of one or more impurities, particularly of N-succinyl tyrosine, in the salt, or in further salts of clavulanic acid, e.g. a pharmaceutically acceptable salt, prepared from the salt.

In a first form of the process of this invention the salt may be washed with the medium, i.e. a wash medium, at a pH of less than 6.5, preferably pH 5.5 or less. The salt may be an amine salt of clavulanic acid, e.g. with any of the amines referred to above, especially tertiary butylamine, and this amine salt may be washed with the wash medium, and then optionally the amine salt may subsequently be converted into a final product pharmaceutically acceptable salt of clavulanic acid, such as an alkali metal salt, e.g. potassium clavulanate. Alternatively the salt which is washed may be a metal salt of clavulanic acid, for example an alkali metal salt of clavulanic acid, particularly potassium clavulanate.

The wash medium may be an aqueous wash medium at such a pH, e.g. acidified water or preferably a mixture of water and a water-miscible organic solvent such as a $C_{1-7}$ alkyl alcohol, typically containing 0.5-20% v:v water, at such a pH. Suitably the aqueous wash medium, e.g. water or such a mixture of water and a water-miscible organic solvent may be acidified with a mineral acid, such as sulphuric, hydrochloric or nitric acid, or an organic e.g. carboxylic acid such as a $C_{1-7}$ alkanoic acid such as acetic acid.

This first form of the process may therefore be a process in which a starting salt of clavulanic acid is provided containing one or more impurity such as N-succinyl tyrosine, and the salt is washed with the wash medium, to thereby produce a product salt of clavulanic acid in which the level of the one or more impurity is lower.

This first form of the process may therefore be a process in which the one or more impurity such as N-succinyl tryosine is removed from a starting salt of clavulanic acid, by washing of the starting salt of clavulanic acid with the wash medium.

In second form of the process of this invention the salt may be recrystallised from the medium at pH of less than 6.5. For example an amine salt may be recrystallised from such a recrystallisation medium, then may subsequently be converted into a final product pharmaceutically acceptable salt of clavulanic acid, such as an alkali metal salt, e.g. potassium clavulanate by known methods such as those referred to above, for example reaction with potassium 2-ethyl hexanoate.

Suitably in this recrystallisation process the salt, e.g. an amine salt may be dissolved in an aqueous medium, e.g. acidified water or a mixture of water and a water-miscible organic solvent such as a $C_{1-7}$ alkyl alcohol. Preferably the solution concentration is high, e.g. e.g. 10-40% or more, but there appears to be no theoretical upper limit. The aqueous medium may initially be at the pH less than 6.5, or the pH may be adjusted when the aqueous solution has been made up, e.g. the aqueous solution may then be acidified with an acid, suitably a mineral acid, such as sulphuric, hydrochloric or nitric acid, or an organic acid e.g. carboxylic acid such as a $C_{1-7}$ alkanoic acid such as acetic acid. A preferred pH is ca. 5.5 or lower.

The salt, e.g. an amine salt, may then be isolated from the aqueous solution. This may be achieved for example by crystallisation by admixing the solution, e.g. an aqueous solution, with a precipitating solvent, such as a water miscible ketone. Suitable ketones include aliphatic ketones, for example a di-$C_{1-7}$ alkyl ketone, acetone being preferred. Solvates of amine clavulanate salts with such ketones are known and an amine salt may precipitate as a ketone solvate. For example the solution may be diluted with an excess, e.g. a 5-50 times excess of the precipitating solvent e.g. of a ketone. Cooling of the diluted solution can help to improve the yield of the precipitated of crystals of the amine salt, e.g. as a solvate, which may be isolated.

This second form of the process may therefore be a process in which a starting salt of clavulanic acid is provided containing one or more impurity such as N-succinyl tyrosine, and the salt is recrystallised in the recrystallisation medium, to thereby produce a product salt of clavulanic acid in which the level of the one or more impurity is lower.

This second form of the process may therefore be a process in which the one or more impurity is removed from a starting salt of clavulanic acid, by recrystallisation of the starting salt of clavulanic acid from the recrystallisation medium.

A third form of the process may be a preparative process in which the salt of clavulanic acid is prepared in a liquid medium at the pH of less than 6.5. For example this third form of the process may comprise a process in which an amine salt of clavulanic salt is prepared by reacting clavulanic acid with an amine in a liquid medium at a pH of less than 6.5. This third form of the process can be used to prepare amine salts of clavulanic acid containing a lower level of impurities such as N-succinyl tyrosine than occur in amine salts of clavulanic acid prepared by alternative or prior art methods.

In a preferred embodiment of this third form of the process the reaction is performed in a two phase system, being an organic solvent phase containing the clavulanic acid, and an aqueous phase into which the amine salt is extracted and which is at the pH of 6.5 or lower. Suitably therefore the aqueous phase may comprise an aqueous solution or suspension of the amine, especially an aqueous solution or suspension of tertiary butylamine. The organic solvent phase is preferably substantially imiscible with water, that is, although some mixing of the solvent with water may occur, over most of the phase diagram two phases are formed.

For example a two phase system may be established, comprising an organic solvent phase containing dissolved clavulanic acid, and a separate aqueous phase, and the organic amine may be introduced into this two phase system, e.g. injected into the aqueous phase, with suitable mixing conditions e.g. agitation or turbulence, so that the amine salt is extracted into the aqueous phase as it is formed. Typically the organic phase may have a concentration of 5-100 g/L, for example 10-40 g/L in clavulanic acid, e.g. ca. 30 g/L. Suitable solvents for the organic phase include substantially water-immiscible $C_{1-7}$ alkyl-$C_{1-7}$ alkanoate esters such as ethyl acetate and tertiary butyl acetate, and di-$C_{1-7}$ alkyl ketones such as methylisobutyl ketone. A temperature of ca. 0-5° C. is preferred for this reaction. Suitably the organic solvent phase may be the product of an extraction by the organic solvent of an optionally pre-purified, e.g. filtered and carbon treated, fermentation broth in which clavulanic acid has been formed.

Suitably the aqueous phase can be provided by back-extraction from the organic solvent phase by a circulating extraction loop so that a high concentration of the amine salt can be built up in the aqueous phase. The aqueous phase may be concentrated to a high concentration, e.g. 25 wt % or more e.g. by circulation of the aqueous extraction loop for a suitable time.

Generally when clavulanic acid is extracted from an aqueous broth to form such an organic extraction phase the broth is acidified to pH below 2.0. Controlled addition of the organic amine into the above-described two phase system can be used to adjust the pH of the aqueous phase, which can be monitored on-line. A preferred pH is again below 5.5.

The amine salt may then be isolated from the aqueous phase. This may be achieved for example by crystallisation by admixing the aqueous solution with a precipitating solvent, such as a water miscible ketone as described above, and this crystallisation can be performed in a manner analogous to the recrystallisation process as described above.

A fourth form of the process of the invention may be a preparative process in which a metal salt of clavulanic acid is formed as a product by a reaction between an amine salt of clavulanic acid and a metal salt precursor compound, in a liquid medium at the pH of less than 6.5. This fourth form of the process can be used to prepare metal salts of clavulanic acid containing a lower level of impurities such as N-succinyl tyrosine than occur in metal salts of clavulanic acid prepared by alternative or prior art methods.

Preferred product metal salts of clavulanic acid which may be prepared in this fourth form of the process are salts of alkali metals and alkaline earth metals, particularly potassium clavulanate.

This fourth form of the process of the invention appears to be suitable for use with all metal salt precursor compounds which can be converted into a pharmaceutically acceptable salt of clavulanic acid by reaction with an amine salt of clavulanic acid. General classes of suitable metal salt precursor compounds include salts of alkali metal cations and alkaline earth metal cations with counter anions which include basic anions, such as hydrogen carbonate, carbonate or hydrogen phosphate, and in particular anions of weak organic carboxylic acids, such as alkanoic acids of formula R—$CO_2H$ where R is $C_{1-20}$ alkyl, for example $C_{1-8}$ alkyl, e.g. salts of acetic, propionic and ethyl hexanoic acid, such as 2-ethyl hexanoic acid. Some examples of precursor compounds in these general classes include sodium or potassium hydrogen carbonate, potassium hydrogen phosphate and calcium carbonate. A preferred metal salt precursor compound for potassium clavulanate is potassium 2-ethylhexanoate.

The reaction of this fourth form of the process of this invention is preferably performed with the amine salt in solution or suspension in a mixture of a water-miscible organic solvent and water, for example a $C_{1-8}$ alkyl alcohol or a mixture of such an alcohol with water, e.g. an isopropanol/water mixture. Suitable proportions for such a solvent:water mixture to suit particular requirements may be determined experimentally, e.g. a solvent:water mixture containing 1-10% v:v water, e.g. ca. 1-5% v:v water. The amine salt may be dissolved in such a solvent which may be either at the pH of 6.0 or less, or which may be adjusted to the pH by addition of a suitable acid, e.g. a mineral acid or organic acid as above. The amine salt may suitably be present in a solution concentration 0.1-1.0M, e.g. ca. 0.5 M in clavulanate moiety. A preferred pH is 5.5 or below, e.g. pH 5.5-5.0.

Although mixing of the amine salt and precursor compound in any order is encompassed by the invention, the metal salt precursor is preferably added to a solution of the amine salt. The precursor may be added as a solution, e.g. in an alcohol, e.g. isopropanol solution. A suitable solution concentration for this precursor compound solution is 0.5-3.5M, e.g. ca. 2M. Slow addition of the precursor solution is preferred, preferably with stirring and preferably being chilled after the addition a temperature below ambient e.g. 0-5° C.

The metal salt of clavulanic acid product may be formed as a precipitate from solution. Precipitation of the product metal salt of clavulanic acid from solution may be encouraged by mixing the solution with a precipitating solvent, e.g. isopropanol, as described above. The solid product can be isolated from the reaction medium by for example filtration and washing of the product.

In each of the above processes the pH of the medium defined above can result in reduction of the quantity of one or more impurities such as N-succinyl tyrosine in the product relative to analogous processes at higher pH.

These processes of the invention may comprise a part of an overall process for preparation of potassium clavulanate from crude clavulanic acid e.g. as formed in a fermentation broth, e.g. in which an amine salt is used as an intermediate.

This overall process may involve the steps of (i) fermentation of a microorganism which produces an aqueous broth containing clavulanic acid, (ii) extraction of the clavulanic acid into an organic solvent, (iii) conversion of the clavulanic acid into an amine salt of clavulanic acid, (iv) exposure of the amine salt to a pH of 6.0 or lower, particularly 5.5 or lower, (v) conversion of the amine salt to potassium clavulanate. The washing and/or recrystallisation processes of the invention may for example be applied to the salts of clavulanic acid prepared as products of either or both of steps (iii) and/or (v). The preparative processes of the invention may for example be applied to either or both of preparation steps (iii) and/or (v), as described above.

In the processes of this invention which involve a pharmaceutically acceptable metal salt of clavulanic acid a preferred salt is potassium clavulanate.

In the processes of this invention which involve an amine salt of clavulanic acid a preferred amine salt is the tertiary butylamine salt of clavulanic acid. This can be made, in a known (see for example EP-A-0 026 044, the content of which is included herein by reference) reaction, by reaction of tertiary butylamine with clavulanic acid, and easily isolated as an acetone solvate. Both the tertiary butylamine salt and its acetone solvate can readily be converted into pharmaceutically acceptable salts of clavulanic acid, e.g. potassium clavulanate, e.g. as disclosed in EP 0026044A. However the processes of the invention appear in principle to be applicable to all those amine salts which are known to be useable as intermediates in the conversion of clavulanic acid into a pharmaceutically acceptable salt such as potassium clavulanate. Consequently these processes of the invention appears in principle to be effective with all such amines.

Examples of such amines, and their corresponding amine salts are disclosed for example in the publications referred to above, and include for example amine poly-, e.g. di-, clavulanate salts if the amine has more than one amino-moiety. Other suitable amine salts include those referred to in the publications mentioned above, e.g. tertiary octylamine, diethylamine, tri-(lower alkyl) amines, dimethylaniline, NN'-diisopropyl-ethylenediamine, tertiary, tertiary diamines such as N,N,N',N'-tetramethyl-1,2-diaminoethane, N,N,N',N'-tetramethyl-1,6-diaminohexane, 1,2-dipiperidinoethane and dipiperidinomethane, diaminoethers such as bis (2-dimethylaminoethyl) ether, benzhydrylamines, N,N'-alkylethylene diamines, such as N,N'-diisopropylethylene diamine, N,N'-diethylene diamine, N,N'-dibenzylethylene diamine, N,N,N',N'-tetramethylene diamine, N,N,N',N'-tetramethylethylene-diamine, 1,3-bis(di-methylamino)-2-propanol, benzhydrylamine and bis (2-(dimethylamino) ethyl) ether, and diisopropylethylendiamine.

The present invention further provides a product amine salt of clavulanic acid being a product of any of the above-described process, particularly tertiarybutylamine clavulanate.

The present invention further provides a product pharmaceutically acceptable metal salt of clavulanic acid being a product of any of the above-described process, particularly potassium clavulanate.

These products are characterised by impurity levels, particularly of N-succinyl tyrosine, which are less than those obtainable via known processes, particularly corresponding process which are carried out in a medium with a pH above that defined.

The invention will now be described by way of example only.

Examples 1, 2 and 3 are expressed in terms of the reduction of the total quantity of impurities in the product salt of clavulanic acid, and Examples 4, 5 and 6 are expressed in terms of reduction of the specific impurity N-succinyl tyrosine.

EXAMPLE 1

Acidification of Amine Salt During Amine Salt Crystallisation 30 g tertiary-butylamine ("t-BA") clavulanate salt was dissolved in water to give a 30% pfa (i.e. calculated as "pure free acid", i.e. clavulanic acid moiety by weight:volume) solution. The pH of the solution was measured and acidified to pH 4.5 with approximately 1.1 ml of 50% sulphuric acid or concentrated nitric acid. A 5× volume of acetone was added and the mixture stirred for 15 minutes. Additional acetone was added over 20 minutes up to 35× the aqueous volume. Throughout the foregoing the amine salt solution was maintained at ambient temperature. The product t-BA salt crystallised and was chilled at 0-5° C. for 60 minutes and collected by filtration. The product was washed with 600 ml of acetone, prior to drying for 12 hours in vacuo. This procedure was repeated at a "natural" pH without acid addition, i.e. ca. pH 7.5. The t-BA salt obtained using these procedures was then converted into product potassium clavulanate using a known method, and levels of total impurities in the potassium clavulanate prepared using the samples of t-BA salt were measured as follows:

| Crystallisation pH of t-BA solution | % total impurities in potassium clavulanate (wrt clav by HPLC) |
|---|---|
| Natural (pH 7.0-7.5) | 2.03 |
| pH 4.5 | 0.03 |

EXAMPLE 2

Preparation of Amine Clavulanate Salt from Clavulanic Acid and Amine Under Acid Conditions 100 L of clavulanic acid aqueous concentrate (ca. 20-40 g/L), from filtered concentrated fermentation broth was solvent extracted at pH 1.5 into methyl isobutyl ketone ("MIBK"). The clavulanic acid rich MIBK was treated with carbon (17 L) and back extracted into water which was adjusted to pH 4.5 by controlled injection of a 50% MIBK solution of t-BA. By controlling the t-BA addition rate the pH of the aqueous phase could be set, and pH 4.5 and pH 5.4 were used in separate experiments. Once the aqueous back extraction solution had reached a suitable crystallisation concentration, a 100 ml aliquot was crystallised by addition of 35 volumes of acetone and the precipitated product isolated as in Example 1 above. The subsequent crystallised amine was converted to potassium salt and analysed for total impurity levels. This was then repeated with an aqueous phase pH of 5.4. By using the pH 4.5 the level of total impurities in the potassium clavulanate was reduced by 50% relative to the level at a pH of 5.4.

EXAMPLE 3

Conversion of an Amine Salt to Potassium Clavulanate 25 g of t-BA clavulanate were dissolved in a mixture of isopropanol (81 ml) and distilled water (10 ml), and the pH was reduced to pH 6.8 with glacial acetic acid. While stirring a further 145 ml of isopropanol was added and 59.5 ml potassium 2-ethylhexanoate (1.92N) dissolved in isopropanol added dropwise over 20 minutes. The so-formed slurry was stirred for 120 minutes in an ice-bath at 0-5° C. and filtered. The potassium clavulanate cake was washed with acetone (120 ml and 200 ml) and dried in vacuo with a nitrogen bleed. Altering the volume of glacial acetic acid added varied the pH of the dissolution solution. Results indicating the effect on the amount of total impurities in the potassium clavulanate ("Kclav") and overall yield of potassium clavulanate are shown in the table below:

| Dissolution pH | % of total impurities in Kclav (wrt clav) |
|---|---|
| 6.8 | 0.87 |
| 6.5 | 0.92 |
| 6.0 | 0.63 |
| 5.5 | 0.57 |
| 5.0 | 0.13 |
| 5.0* | 0.11 |

*The volume of water was reduced to compensate for the additional volume of acetic acid used.

The experiments described in Example 3 above were repeated using other acids than acetic acid to achieve the specified pH, for example hydrochloric acid was used with similar results.

EXAMPLE 4

Acidification of Amine Salt During Amine Salt Crystallisation 30 g tertiary-butylamine ("t-BA") clavulanate salt was dissolved in water to give a 30% pfa (i.e. calculated as "pure free acid", i.e. clavulanic acid moiety by weight:volume) solution. The pH of the solution was measured and acidified to pH 4.5 with approximately 1.1 ml of 50% sulphuric acid or concentrated nitric acid. A 5× volume of acetone was added and the mixture stirred for 15 minutes. Additional acetone was added over 20 minutes up to 35× the aqueous volume. Throughout the foregoing the amine salt solution was maintained at ambient temperature. The product t-BA salt crystallised and was chilled at 0-5° C. for 60 minutes and collected by filtration. The product was washed with 600 ml of acetone, prior to drying for 12 hours in vacuo. This procedure was repeated at a "natural" pH without acid addition, i.e. ca. pH 8.5. The level of N-succinyl tyrosine in the t-BA salt obtained using these procedures was then measured as follows:

| Crystallisation pH of t-BA solution | % N-succinyl tyrosine in t-BA clavulanate (wrt clav by HPLC) |
|---|---|
| Natural (pH 8.5) | 3.48 |
| pH 4.5 | 0.03 |

EXAMPLE 5

Preparation of Amine Clavulanate Salt from Clavulanic Acid and Amine Under Acid Conditions 100 L of clavulanic acid aqueous concentrate (ca. 2040 g/L), from filtered concentrated fermentation broth was solvent extracted at pH 1.5 into methyl isobutyl ketone ("MIBK"). The clavulanic acid rich MIBK was treated with carbon (17 L) and back extracted into water which was adjusted to pH 4.5 by controlled injection of a 50% MIBK solution of t-BA. By controlling the t-BA addition rate the pH of the aqueous phase could be set, and pH 4.5 and pH 5.4 were used in separate experiments. Once the aqueous back extraction solution had reached a suitable crystallisation concentration, a 100 ml aliquot was crystallised by addition of 35 volumes of acetone and the precipitated product isolated as in Example 1 above. The subsequent crystallised amine was converted to potassium salt and analysed for N-succinyl tyrosine levels. This was then repeated with an aqueous phase pH of 5.4. By using the pH 4.5 the level of N-succinyl tyrosine impurity in the potassium clavulanate was reduced 26-fold relative to the level at a pH of 5.4.

EXAMPLE 6

Conversion of an Amine Salt to Potassium Clavulanate 25 g of t-BA clavulanate were dissolved in a mixture of isopropanol (81 ml) and distilled water (10 ml), and the pH was reduced to pH 6.8 with glacial acetic acid. While stirring a further 145 ml of isopropanol was added and 59.5 ml potassium 2-ethylhexanoate (1.92N) dissolved in isopropanol added dropwise over 20 minutes. The so-formed slurry was stirred for 120 minutes in an ice-bath at 0-5° C. and filtered. The potassium clavulanate cake was washed with acetone (120 ml and 200 ml) and dried in vacuo with a nitrogen bleed. Altering the volume of glacial acetic acid added varied the pH of the dissolution solution. Results indicating the effect on the amount of N-succinyl tyrosine impurity in the potassium clavulanate ("Kclav") and overall yield of potassium clavulanate are shown in the table below:

| Dissolution pH | % of N-succinyl tyrosine in Kclav (wrt clav) |
|---|---|
| 6.8 | 0.62 |
| 6.5 | 0.65 |
| 6.0 | 0.44 |
| 5.5 | 0.40 |
| 5.0 | 0.04 |
| 5.0* | 0.07 |

*The volume of water was reduced to compensate for the additional volume of acetic acid used.

The experiments described in Example 3 above were repeated using other acids than acetic acid to achieve the specified pH, for example hydrochloric acid was used with similar results.

The invention claimed is:

1. A process for the preparation of a pharmaceutically acceptable metal salt of clavulanic acid from an amine salt of clavulanic acid, comprising washing the amine salt of clavulanic acid in a wash medium, or recrystallisation of the amine salt of clavulanic acid from a recrystallization medium, or preparation of an amine salt of clavulanic acid by reacting clavulanic acid with an amine in a liquid preparation medium followed by conversion of the amine salt to said pharmaceutically acceptable metal salt, wherein the wash medium or the recrystallization medium, or the preparation medium is at a pH of 3.5-5.5.

2. A process according to claim 1 wherein the amine salt is washed with a wash medium at a pH of 3.5-5.5.

3. A process according to claim 2 wherein the wash medium is a mixture of water and a water-miscible organic solvent at a pH of 3.5-5.5.

4. A process according to claim 2, comprising a process in which the amine salt of clavulanic acid is provided containing N-succinyl tyrosine as an impurity, and the salt is washed with the wash medium, to thereby produce a product salt of clavulanic acid in which the level of the N-succinyl tyrosine impurity is lower.

5. A process according to claim 1 wherein the_amine salt of clavulanic acid is recrystallized from a recrystallization medium at pH-of 3.5-5.5.

6. A process according to claim 5 wherein the amine salt is dissolved in an aqueous medium at the pH of 3.5-5.5, or which is subsequently adjusted to pH of 3.5-5.5, then the salt is isolated from the aqueous solution by crystallization by admixing the solution with a precipitating solvent.

7. A process according to claim 5, comprising a process in which the amine salt of clavulanic acid is provided containing N-succinyl tyrosine as an impurity, and the amine salt is recrystallized from the recrystallization medium, to thereby produce a product amine salt of clavulanic acid in which the level of the N-succinyl tyrosine impurity is lower.

8. A process according to claim 1, comprising a preparative process in which the amine salt of a clavulanic acid is prepared in a liquid medium at a pH of 3.5-5.5.

9. A process according to claim 8, comprising preparation of an amine salt of clavulanic salt by reacting clavulanic acid with an amine in a liquid medium at a pH of 3.5-5.5.

10. A process according to claim 9 performed in a two phase system, having an organic phase and an aqueous phase, the organic phase containing an organic solvent and the clavulanic acid, and the aqueous phase into which the amine salt is extracted and which is at the pH of 3.5-5.5.

11. A process according to claim 1 wherein the pharmaceutically acceptable metal salt of clavulanic acid is potassium clavulanate.

12. A process according to claim 1 wherein the amine salt of clavulanic acid is tertiary butylamine clavulanate.

13. A process according to claim 9 wherein the pharmaceutically acceptable metal salt of clavulanic acid is potassium clavulanate and the amine salt of clavulanic acid is tertiary butylamine clavulanate prepared by reacting the clavulanic acid with tertiary butylamine.

14. A process according to claim 10 wherein the organic solvent is selected from $C_{1-7}$alkyl-$C_{1-7}$ alkanoate esters and di-$C_{1-7}$ alkyl ketones.

15. A process according to claim 10 wherein the aqueous phase is provided by extraction into the aqueous phase from the organic solvent phase by a circulating extraction loop so that a concentration of 25 wt % or more of the amine salt is built up in the aqueous phase.

16. A process according to claim 10 wherein the amine salt is isolated from the aqueous phase by crystallization by admixing the aqueous solution with a water miscible ketone.

* * * * *